(12) United States Patent
Boone et al.

(10) Patent No.: US 12,070,609 B2
(45) Date of Patent: Aug. 27, 2024

(54) ELECTRICAL COMPONENT AND METHOD OF FORMING SAME

(71) Applicant: Medtronic, Inc., Minneapolis, MN (US)

(72) Inventors: Mark R. Boone, Gilbert, AZ (US); Joachim Hossick-Schott, Minneapolis, MN (US); Mark Henschel, Phoenix, AZ (US)

(73) Assignee: Medtronic, Inc., Minneapolis, MN (US)

(*) Notice: Subject to any disclaimer, the term of this patent is extended or adjusted under 35 U.S.C. 154(b) by 566 days.

(21) Appl. No.: 17/367,826

(22) Filed: Jul. 6, 2021

(65) Prior Publication Data

US 2022/0037090 A1 Feb. 3, 2022

Related U.S. Application Data

(60) Provisional application No. 63/058,896, filed on Jul. 30, 2020.

(51) Int. Cl.
| | | |
|---|---|---|
| *A61N 1/375* | (2006.01) | |
| *H01G 9/035* | (2006.01) | |
| *H01G 9/04* | (2006.01) | |
| *H01G 9/042* | (2006.01) | |
| *H01G 9/15* | (2006.01) | |

(52) U.S. Cl.
CPC ........... *A61N 1/375* (2013.01); *A61N 1/3758* (2013.01); *H01G 9/0425* (2013.01); *H01G 9/15* (2013.01); *H01G 9/035* (2013.01); *H01G 2009/05* (2013.01)

(58) Field of Classification Search
CPC .... A61N 1/375; A61N 1/3758; H01G 9/0425; H01G 9/15; H01G 9/035; H01G 2009/05
See application file for complete search history.

(56) References Cited

U.S. PATENT DOCUMENTS

| | | | |
|---|---|---|---|
| 5,812,366 A * | 9/1998 | Kuriyama | H01G 9/15 361/523 |
| 6,510,044 B1 | 1/2003 | Loeffelholz et al. | |
| 6,511,588 B1 * | 1/2003 | Kobayashi | H01L 21/2885 257/E21.585 |
| 8,199,461 B2 | 6/2012 | Zednicek et al. | |
| 8,992,635 B2 | 3/2015 | Otterstedt | |

(Continued)

FOREIGN PATENT DOCUMENTS

JP 2000114113 4/2000

*Primary Examiner* — Michael P McFadden
(74) *Attorney, Agent, or Firm* — Mueting Raasch Group

(57) ABSTRACT

Various embodiments of an electrical component and a method of forming such component are disclosed. The electrical component includes a substrate having a first major surface, a second major surface, and cavity disposed in the substrate. The cavity extends between the first major surface and a recessed surface. Tantalum material is disposed within the cavity. Further, the tantalum material includes tantalum particles. The electrical component also includes a dielectric layer disposed on the tantalum particles and an electrolyte cathode layer disposed on the dielectric layer. The electrical component further includes a cathode electrode disposed on the electrolyte cathode layer and over the cavity.

20 Claims, 11 Drawing Sheets

(56) References Cited

U.S. PATENT DOCUMENTS

| | | |
|---|---|---|
| 2003/0218859 A1* | 11/2003 | Yoshida ................ H01G 9/052 |
| | | 361/528 |
| 2005/0280978 A1 | 12/2005 | Sakaguchi et al. |
| 2010/0020473 A1 | 1/2010 | Prymak et al. |
| 2012/0300369 A1 | 11/2012 | Lee et al. |
| 2016/0284476 A1 | 9/2016 | Paulus et al. |
| 2017/0069775 A1* | 3/2017 | Fenner ................ H01L 31/055 |
| 2017/0172505 A1 | 6/2017 | Ruben et al. |
| 2018/0363158 A1* | 12/2018 | Religieux .............. C25D 7/123 |
| 2020/0154567 A1 | 5/2020 | Kim et al. |

\* cited by examiner

ELECTRICAL COMPONENT AND METHOD OF FORMING SAME

RELATED PATENT APPLICATIONS

This application claims the benefit of U.S. Provisional Patent Application Ser. No. 63/058,896, filed on Jul. 30, 2020, which is incorporated by reference herein in its entirety.

TECHNICAL FIELD

This disclosure generally relates to electrical components. In particular, this disclosure relates to electrical components suitable for use in implantable devices.

BACKGROUND

A wide variety of electronic assemblies such as those that are utilized for implantable medical devices (IMDs) employ electronic circuitry, e.g., for providing electrical stimulation of body tissue and/or monitoring a physiologic condition. Such IMDs can deliver electrical therapy energy in the form of shocking energy and stimulating pulses to selected body tissue and typically include output circuitry for providing the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), are typically formed having a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past 20 years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers. The high voltage output circuitry has also been improved in many respects to provide monophasic, biphasic, or multi-phase cardioversion/defibrillation shock or pulse waveforms that are efficacious, sometimes with particular combinations of cardioversion/defibrillation electrodes.

The miniaturization of IMDs is driving size and cost reduction of all IMD components, including the electronic circuitry components, where it is desirable to increase the density and reduce the size of such components so that the overall circuitry can be more compact. As the dimensions of IMDs decrease, the electronic circuits of the IMD are formed as integrated circuits to fit within a minimal space. Furthermore, as the dimensions of the components are also being reduced, it is desirable to improve the use of the available space within the IMD package.

Electronic circuitry for IMDs and other electronic devices can include one or more capacitors. Such capacitors are passive components that store potential energy in an electric field and are designed to add capacitance to circuits. Various types of capacitors can be utilized, including ceramic and electrolytic capacitors. Tantalum capacitors are a type of electrolytic capacitor that have a relatively high capacitance density compared to other capacitors such as ceramic capacitors.

SUMMARY

The techniques of this disclosure generally relate to electrical components and methods for forming such electrical components. In one or more embodiments, an electrical component can include tantalum material disposed within a cavity of a substrate and a cathode electrode disposed over the cavity of the substrate. The tantalum material can include tantalum particles. The electrical component can also include a dielectric disposed on the tantalum particles and an electrolyte cathode layer disposed on the dielectric. In one or more embodiments, the electrical component can form a capacitor that can be utilized in any suitable electronic circuit or device.

In one example, aspects of this disclosure relate to an electrical component that includes a substrate having a first major surface, a second major surface, and a cavity disposed in the substrate. The cavity extends between the first major surface and a recessed surface. Tantalum material is disposed within the cavity. Further, the tantalum material includes tantalum particles. The electrical component also includes a dielectric layer disposed on the tantalum particles and an electrolyte cathode layer disposed on the dielectric layer. The electrical component further includes a cathode electrode disposed over the cavity.

In another example, aspects of this disclosure relate to a method that includes disposing a cavity in a substrate that extends between a first major surface and a recessed surface, disposing tantalum material including tantalum particles in the cavity, disposing a dielectric layer on the tantalum particles, disposing an electrolyte cathode layer on the dielectric layer, and disposing a cathode electrode on the electrolyte cathode layer and over the cavity.

In another example, aspects of this disclosure relate to an implantable medical device that includes a housing and an electronic assembly within the housing. The electronic assembly includes an electrical component that includes a substrate having a first major surface, a second major surface, and a cavity disposed in the substrate. The cavity extends between the first major surface and a recessed surface. Tantalum material is disposed within the cavity. Further, the tantalum material includes tantalum particles. The electrical component also includes a dielectric layer disposed on the tantalum particles and an electrolyte cathode layer disposed on the dielectric layer. The electrical component further includes a cathode electrode disposed over the cavity.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The details of one or more aspects of the disclosure are set forth in the accompanying drawings and the description herein. Other features, objects, and advantages of the techniques described in this disclosure will be apparent from the description and drawings, and from the claims.

DETAILED DESCRIPTION

The techniques of this disclosure generally relate to electrical components and methods for forming such electrical components. In one or more embodiments, the electrical component can include tantalum material including tantalum particles disposed within a cavity of a substrate, a dielectric layer disposed on the tantalum particles, an electrolyte cathode layer disposed on the dielectric layer, and a cathode electrode disposed over the cavity. An anode electrode can be disposed over the first major surface or on the second major surface of the substrate. In one or more embodiments, the electrical component can form a capacitor that can be utilized in any suitable electronic circuit or device.

In general, the present disclosure provides various embodiments of apparatuses, systems, and associated techniques that relate to electrical components. Such electrical components can include any suitable components or circuitry, e.g., capacitors, tantalum capacitors, etc. Tantalum capacitors can be desirable for their reliability and capacitance density. Because of their dimensions, tantalum capacitors are typically disposed on surfaces of integrated circuit boards. At thicknesses greater than 1 mm, typical tantalum capacitors add significantly to the size and thickness of these integrated circuit boards.

One or more embodiments of electrical components described herein can have a thickness, e.g., of no greater than 600 micrometers. Because of this decreased thickness, one or more electrical components described herein can be embedded within an integrated circuit board or integrated into a substrate, thereby enabling smaller electronic packages and assemblies. One or more embodiments of electrical components described herein can have a thickness, e.g., of no greater than 1 millimeter. Such electrical components can be surface mounted.

Figure 1:
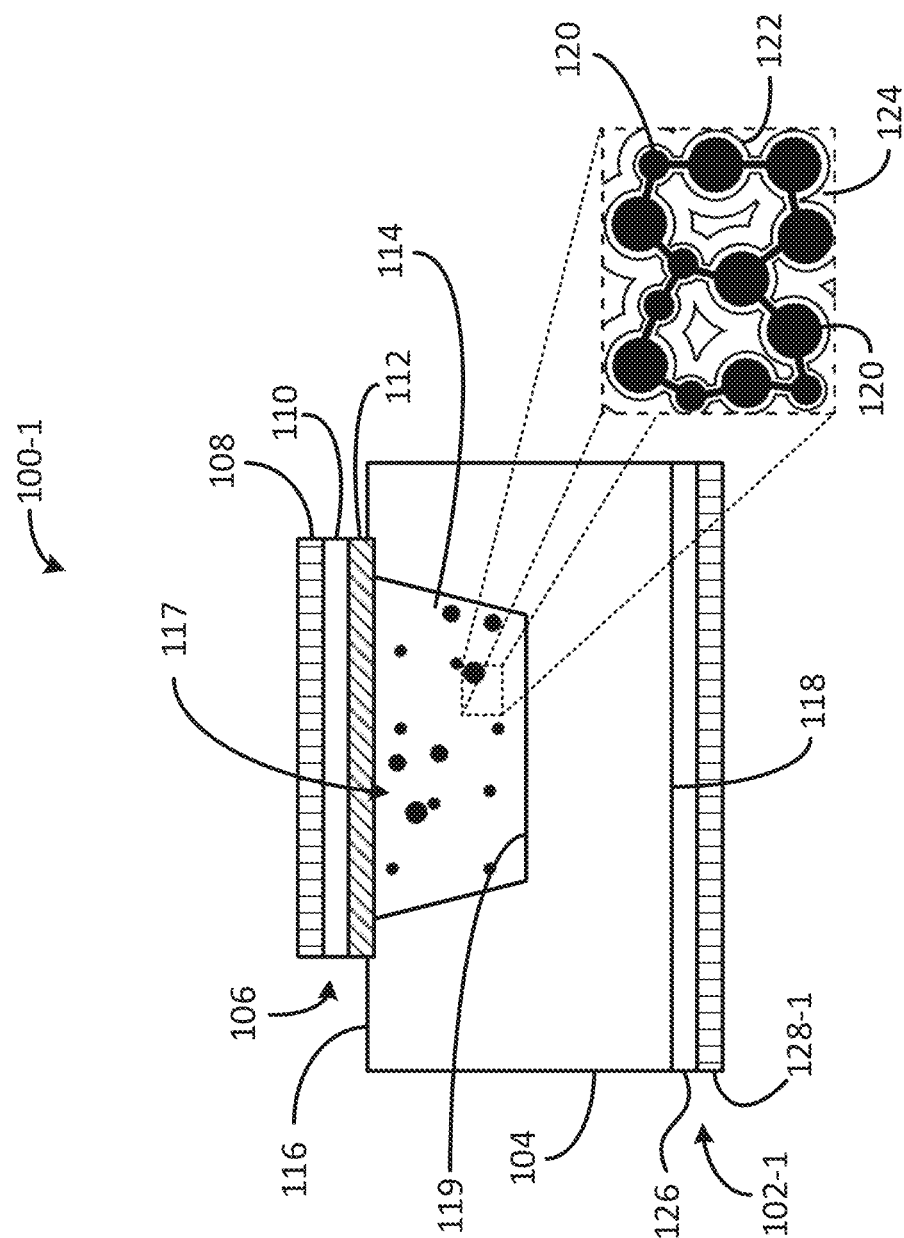
FIG. 1 is a schematic cross-section view of one embodiment of an electrical component.

FIG. 1 is a schematic cross-section view of one embodiment of an electrical component 100-1. Electrical component 100-1 includes a substrate 104 having a first major surface 116, a second major surface 118, and a cavity 117 disposed in the substrate and extending between the first major surface 116 and a recessed surface 119. The electrical component 100-1 also includes tantalum material 114 disposed within the cavity 117, where the tantalum material includes tantalum particles 120. Further, the electrical component 100-1 includes an anode electrode 102-1 disposed on the second major surface 118 of the substrate 104 and a cathode electrode 106 disposed on the first major surface 116 of the substrate and over the cavity 117.

The electrical component 100-1 can be utilized in any suitable device or electrical circuitry, e.g., printed circuit boards, integrated circuit packages, substrates, glass substrates, ceramic substrates, sapphire substrates, silicon substrates, etc. Further, the electrical component 100-1 can exhibit any suitable characteristics. For example, the electrical component 100-1 can include any suitable amount of tantalum by volume of the electrical component. Further, the electrical component 100-1 can have any suitable dimensions. In one or more embodiments, the electrical component 100-1 can have a height or thickness as measured in a direction orthogonal to the first and second major surfaces 116, 118 of the substrate 104 of no greater than 500 micrometers.

The substrate 104 can include any suitable dimensions and take any suitable shape. Further, the substrate 104 can include any suitable material or materials. In one or more embodiments, the substrate 104 includes any suitable conductive material, e.g., tantalum foil, metal foil, metal alloy foil, etc. In one or more examples, the substrate 104 is annealed tantalum foil. The substrate 104 may be provided in any suitable size and any suitable thickness. In one or more embodiments, the substrate 104 may have a height or thickness extending from the first major surface 116 to the second major surface 118 from 50 micrometers to 300 micrometers. In one or more embodiments, the thickness of the substrate 104 extending from the first major surface 116 to the second major surface 118 may be up to 1000 micrometers. For example, the thickness of the substrate 104 extending from the first major surface 116 to the second major substrate 118 may be equal to or less than 1000 micrometers, equal to or less than 950 micrometers, equal to or less than 900 micrometers, equal to or less than 850 micrometers, equal to or less than 800 micrometers, equal to or less than 750 micrometers, equal to or less than 700 micrometers, equal to or less than 650 micrometers, equal to or less than 600 micrometers, equal to or less than 550 micrometers, equal to or less than 500 micrometers, equal to or less than 450 micrometers, equal to or less than 400 micrometers, equal to or less than 350 micrometers, equal to or less than 300 micrometers, equal to or less than 250 micrometers, equal to or less than 200 micrometers, equal to or less than 150 micrometers, or equal to or less than 100 micrometers.

Disposed in the substrate 104 and extending between the first major surface 116 and the recessed surface 119 of the substrate is the cavity 117. The cavity 117 can include any suitable dimensions and take any suitable shape or shapes. Further, the cavity 117 can be disposed in the substrate 104 using any suitable technique or techniques, e.g., wet etching, dry etching, mechanical etching, laser etching, etc. In one or more embodiments, the one or more cavities 117 may have a depth measured from the first major surface 116 to the recessed surface 119 that is 20 percent to 90 percent of the thickness of the substrate 104. Although illustrated as including one cavity 117, the electrical component 100-1 can include any suitable number of cavities as is further described herein.

Disposed within the cavity 117 is the tantalum material 114, which fills at least a portion of the cavity. In one or more embodiments, the size and shape of the tantalum material 114 is determined by the size and shape of the cavity 117. Tantalum material 114 includes tantalum particles 120. Any suitable tantalum particles 120 can be utilized in the tantalum material 114. Further, the tantalum particles 120 can have any suitable dimensions.

The tantalum particles 120 can be electrically and mechanically coupled together using any suitable technique or techniques. In one or more embodiments, the tantalum particles 120 can be sintered together using any suitable technique or techniques, e.g., heating, laser, microwave, spark plasma, etc. Further, the tantalum material 114 can be disposed within the cavity 117 using any suitable technique or techniques, e.g., deposition, printing, stencil printing, dispensing, jetting, etc. In one or more embodiments, the tantalum material 114 can include tantalum paste. Such tantalum paste can include binding agents to hold the tantalum particles 120 together. The tantalum paste can include any suitable binding agents, e.g., organic binders, solvents, etc.

The tantalum material 114 can further include a dielectric layer 122 disposed on one or more of the tantalum particles 120. In one or more embodiments, the dielectric layer 122 can be disposed on substantially all of the tantalum particles 120. The dielectric layer 122 can include any suitable dielectric material or materials, e.g., tantalum pentoxide. Further, the dielectric layer 122 can be formed using any suitable technique or techniques, e.g., anodization, wetforming, atomic layer deposition, annealing, etc.

Further, the tantalum material 114 can also include an electrolyte cathode layer 124 disposed on the dielectric layer 122. The electrolyte cathode layer 124 can include any suitable material or materials, e.g., manganese dioxide, conductive polymer, etc. Further, the electrolyte cathode layer 124 can include any suitable dimensions and take any suitable shape or shapes. The electrolyte cathode 124 layer can be formed using any suitable technique or techniques, e.g., pyrolysis, impregnation, printing, etc.

The electrical component 100-1 can also include the anode electrode 102-1, which is disposed on the second major surface 118 of the substrate 104. Further, the anode electrode 102-1 can include any suitable electrically conductive material or materials, e.g., copper, gold, silver, tantalum, graphite, aluminum, chrome, carbon, etc. The anode electrode 102-1 can include any suitable dimensions and take any suitable shape or shapes. Further, the anode electrode 102-1 can be formed using any suitable technique or techniques, e.g., deposition, chemical vapor deposition, physical vapor deposition, sputtering, electroplating, printing, dispensing, etc.

The anode electrode 102-1 can include one or more layers. In one or more embodiments, the anode electrode 102-1 can include an anode connector layer 126 disposed on the second major surface 118 of the substrate 104. The anode connector layer 126 can include any suitable dimensions and take any suitable shape or shapes. The anode connector layer 126 can be formed using any suitable technique or techniques, e.g., deposition, PVD, CVD, sputtering, electroplating, foil lamination, etc. Further, the anode connector layer 126 can include suitable material or materials, e.g., at least one of copper, gold, silver, aluminum, or carbon, or other conductive material.

In one or more embodiments, the anode electrode 102-1 can include an anode conductor layer 128 disposed on the anode connector layer 126. The anode conductor layer 128 can also include any suitable dimensions and take any suitable shape or shapes. The anode conductor layer 128 can be formed using any suitable technique or techniques, e.g., deposition, PVD, CVD, sputtering, electroplating, foil lamination, etc. The anode conductor layer 128 can include any suitable electrically conductive material or materials, e.g., copper, gold, silver, aluminum, or other conductive material.

Disposed on the electrolyte cathode layer 124 and over the cavity 117 of the substrate 104 is the cathode electrode 106. The cathode electrode 106 can also be disposed on the first major surface 116 of the substrate. The cathode electrode 106 can include any suitable dimensions and take any suitable shape or shapes. The cathode electrode 106 can include any suitable electrically conductive material or materials, e.g., the same electrically conductive materials described herein regarding the anode electrode 102-1. The cathode electrode 106 can include one or more layers. The cathode electrode 106 can be formed using any suitable technique, e.g., the same technique or techniques described herein regarding the anode electrode 102-1.

In one or more embodiments, the cathode electrode 106 can include a cathode connection layer 112 disposed on the first major surface 116 of the substrate 104 and over the cavity 117. The cathode connection layer 112 can include any suitable electrically conductive material or materials, e.g., the same electrically conductive materials described herein regarding the anode electrode 102-1. Further, the cathode connection layer 112 can include any suitable dimensions and take any suitable shape or shapes. The cathode connection layer 112 can be formed using any suitable technique or techniques, e.g., the same technique or techniques described herein regarding the anode electrode 102-1.

In one or more embodiments, the cathode electrode 106 can include a cathode conductor layer 110 disposed on the cathode connection layer 112. The cathode conductor layer 110 can include any suitable electrically conductive material or materials, e.g., the same electrically conductive materials described herein regarding the anode electrode 102-1. Further, the cathode conductor layer 110 can include any suitable dimensions and take any suitable shape. The cathode conductor layer 110 can be formed using any suitable technique or techniques, e.g., the same technique or techniques described herein regarding the anode electrode 102-1. In one or more embodiments, the cathode conductor layer 110 can be patterned using any suitable technique or techniques to provide a patterned conductive layer.

In one or more embodiments, the cathode electrode 106 can optionally include a cathode packaging layer 108 disposed on the cathode conductor layer 110. The cathode packaging layer 108 can include any suitable electrically conductive material or materials, e.g., the same electrically conductive materials described herein regarding the anode electrode 102-1. Further, the cathode packaging layer 108 can include any suitable dimensions and take any suitable shape. The cathode packaging layer 108 can be formed using any suitable technique or techniques, e.g., the same technique or techniques described herein regarding the anode electrode 102-1. In one or more embodiments, the cathode packaging layer 108 can be patterned using any suitable technique or techniques to provide a patterned conductive layer. The cathode packaging layer 108 may include one or more layers as may be suitable for subsequent packaging of the electrical component 100-1, e.g., embedding in a printed circuit board.

Figure 2:
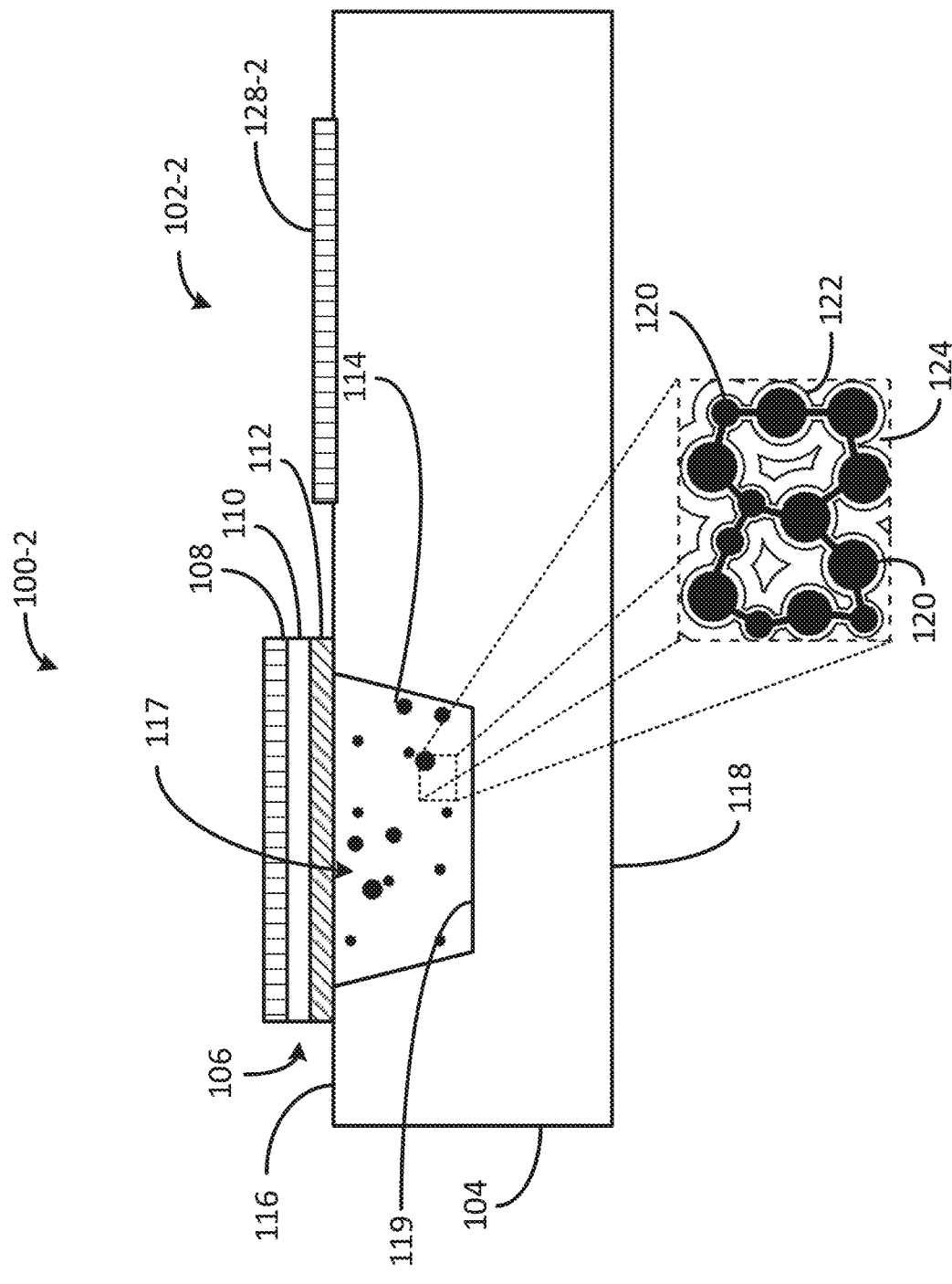
FIG. 2 is a schematic cross-section view of another embodiment of an electrical component.

FIG. 2 is a schematic cross-section view of another embodiment of an electrical component 100-2. All of the design considerations and possibilities regarding the electrical component 100-1 of FIG. 1 apply equally to the electrical component 100-2 of FIG. 2. Electrical component 100-2 includes a substrate 104 having a first major surface 116, a second major surface 118, and a cavity 117 disposed in the substrate and extending between the first major surface 116 and a recessed surface 119. The electrical component 100-2 also includes tantalum material 114 disposed within the cavity 117, where the tantalum material includes tantalum particles 120. Further, the electrical component 100-2 includes an anode electrode 102-2 disposed on the first major surface 116 of the substrate 104 and a cathode electrode 106 disposed on an electrolyte cathode layer 124 over the cavity 117.

One difference between the electrical component 100-2 and the electrical component 100-1 is that an anode electrode 102-2 is disposed on the first major surface 116 of the substrate 102. The anode electrode 102-2 can include anode conductor layer 128-2 disposed on the first major surface 116 of the substrate 104. The anode conductor layer 128-2 can include any suitable material or materials and be formed using any suitable technique or techniques, e.g., the same materials and techniques described herein with regard to the anode pad 128-1 of FIG. 1. The anode conductor layer 128-2 can take on any suitable shape and have any suitable dimensions. Although not shown, the electrical component 100-2 can optionally include the anode electrode 102-1 of electrical component 100-1 disposed on the second major surface 118 of the substrate 104 in addition to the anode electrode 102-2.

Figure 3:
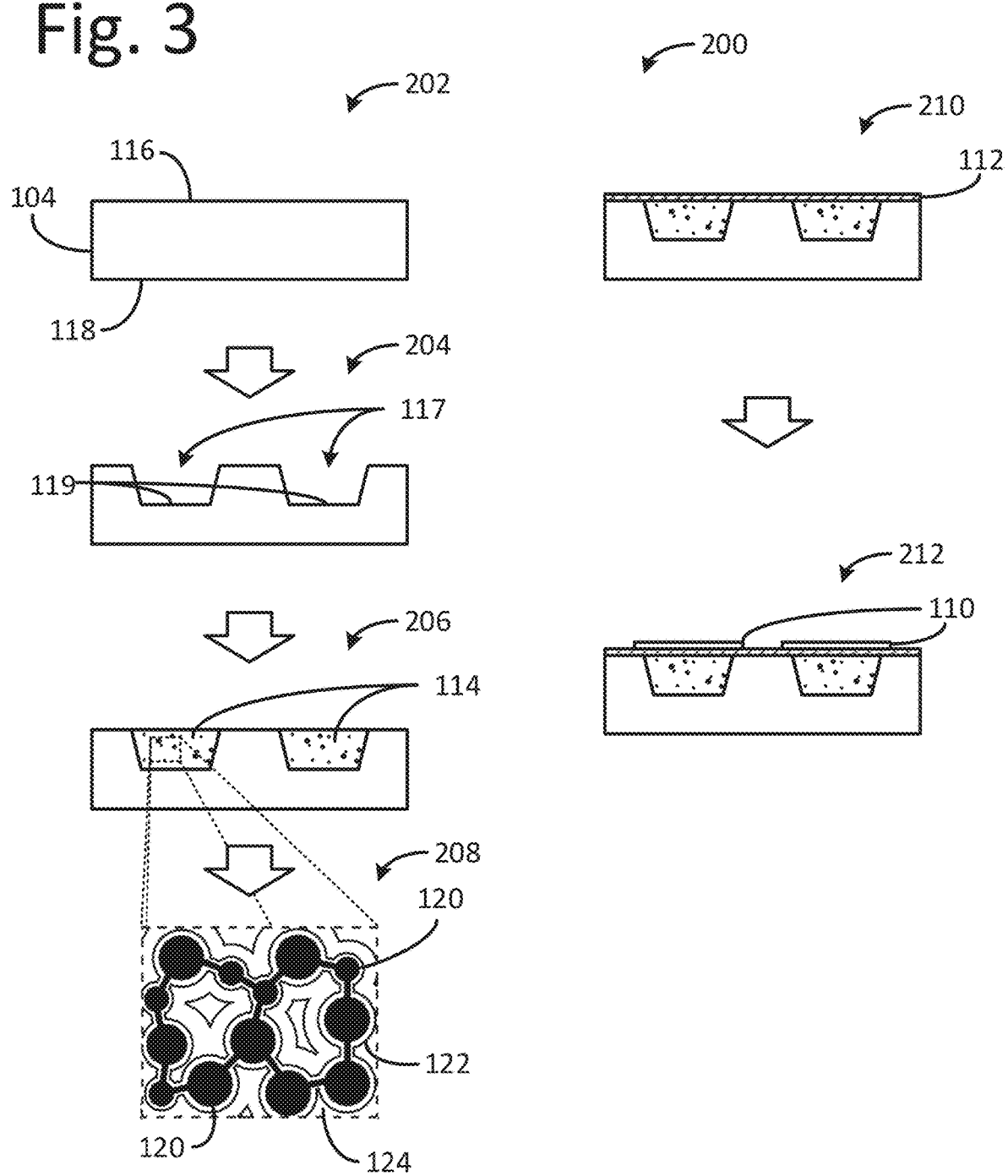
FIG. 3 is a schematic flow diagram of a first portion of a process for forming the electrical components of FIGS. 1 and 2.
Figure 4:
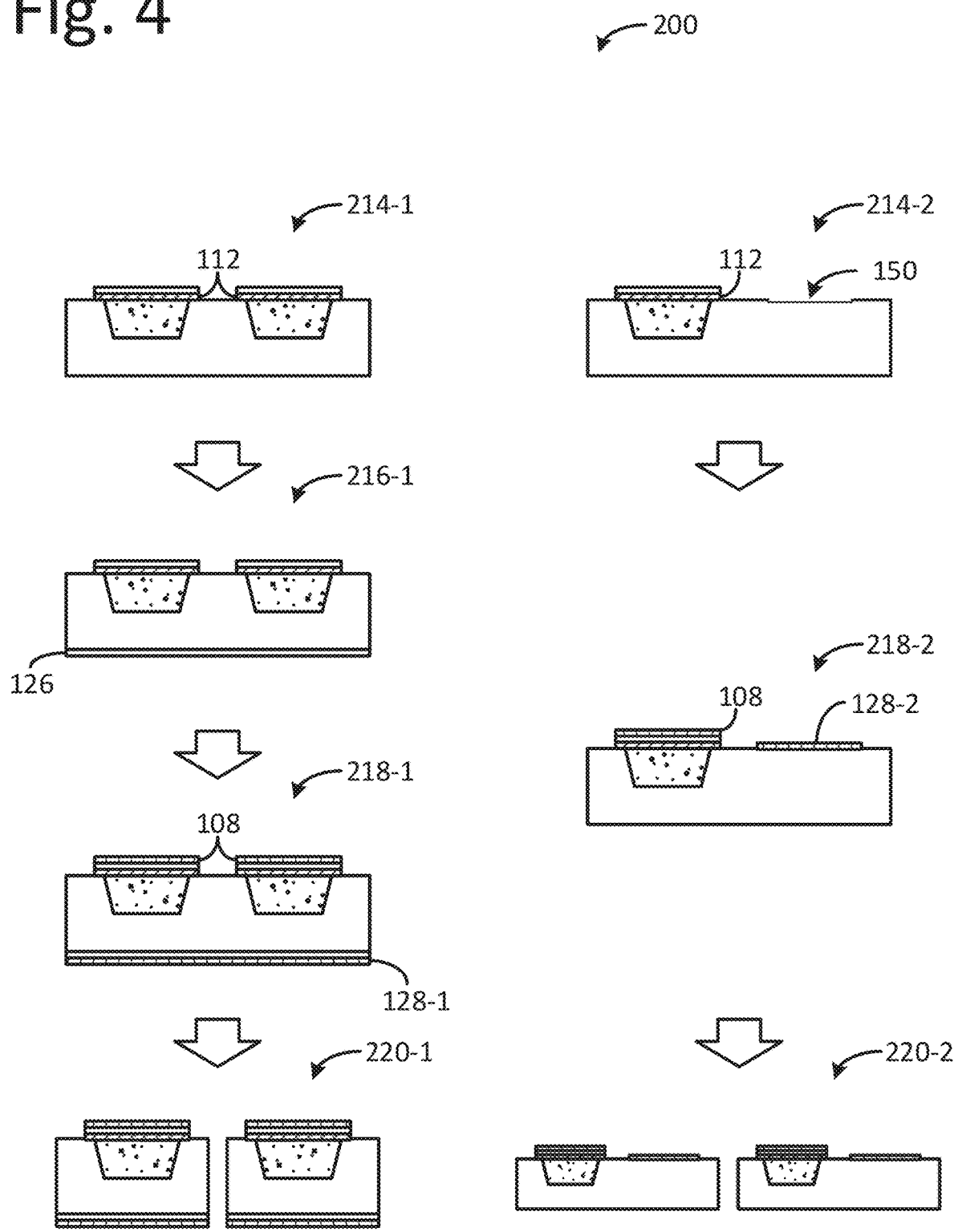
FIG. 4 is a schematic flow diagram of a second portion of a process for forming the electrical components of FIGS. 1 and 2.

The electrical components 100-1 and 100-2 can be manufactured utilizing any suitable technique or techniques. For example, FIGS. 3 and 4 are schematic flow diagrams of first and second portions of one embodiment of a method 200 of forming a plurality of electrical components 100-1 or 100-2. Although described in reference to electrical components 100-1 and 100-2 of FIGS. 1 and 2, the method 200 can be utilized to form any suitable electrical component.

At 202, the substrate 104 is provided. The substrate 104 includes the first major surface 116 and the second major surface 118 opposite the first major surface. The substrate 104 can include any suitable conductive material, e.g., tantalum foil, metal foil, metal alloy foil, etc. In one or more examples, the substrate 104 is annealed tantalum foil. The substrate 104 can be provided in any suitable size and any suitable thickness. In one or more embodiments, the substrate 104 may be provided at a thickness between 50 micrometers to 300 micrometers.

At 204, one or more cavities 117 can be disposed in the first major surface 116 of the substrate 104 using any suitable technique or techniques. In one or more embodiments, the one or more cavities 117 may be roll-formed. In one or more embodiments, the one or more cavities 117 may be coined into the substrate 104. Additional techniques for disposing one or more cavities 117 in the substrate 104 may include etching, pressing, stamping, embossing, etc. Each of the one or more cavities 117 may extend from the first major surface 116 to the recessed surface 119. The one or more cavities 117 may have a depth measured from the first major surface 116 to the recessed surface 119 that is 20 percent to 90 percent of the thickness of the substrate 104.

At 206, the tantalum material 114 including tantalum particles 120 can be disposed within the one or more cavities 117 of the substrate 104 using any suitable technique or techniques. The tantalum material may include, e.g., tantalum powder, a tantalum slug, tantalum paste, etc. In embodiments where the tantalum material 114 includes tantalum paste, the tantalum paste can be dried and debindered using any suitable technique or techniques at 206, for example, heating the tantalum paste.

In one or more embodiments, the tantalum material 114 can be sintered at 206 using any suitable technique or techniques. Sintering the tantalum material 114 can cause the tantalum particles 120 to at least partially fuse together to form one or more mechanical and electrical connections between the tantalum particles. Additionally, sintering can cause one or more of the tantalum particles 114 to fuse to the substrate 104, forming at least one mechanical or electrical connection between the tantalum material and the substrate. In one or more embodiments, the tantalum material 114 can be sintered by heating the material to a temperature of at least 1200 degrees Celsius and no greater than 3000 degrees Celsius.

At 208, the dielectric layer 122 can be disposed on the tantalum particles 120 using any suitable technique or techniques. In one or more embodiments, the dielectric layer 122 may be disposed using, e.g., anodization, wet-forming, atomic layer deposition, annealing, etc. The dielectric layer 122 can include any suitable dielectric material or materials, e.g., tantalum pentoxide. Further, at 208, the electrolyte cathode layer 124 can be disposed on the dielectric layer 122 using any suitable technique or techniques. In one or more embodiments, the electrolyte cathode layer 124 may be disposed using, e.g., pyrolysis, impregnating, printing, dispensing, dip-coating, etc. The electrolyte cathode layer 124 can include any suitable material or materials, e.g., manganese dioxide, conductive polymer, etc.

At 210, the cathode connection layer 112 can be disposed on the first major surface 116 of the substrate 104 and over the one or more cavities 117 using any suitable technique or techniques, e.g., deposition, PVD, CVD, sputtering, electroplating, foil lamination, etc. At 212, the cathode conductor layers 110 are disposed on the cathode connection layer 112 using any suitable technique or techniques, e.g., deposition, PVD, CVD, sputtering, electroplating, foil lamination, shadow masking, etc.

In FIG. 4, the process 200 can include any of steps 214-1, 214-2, 216-1, 218-1, 218-2, 220-1, and 220-2. For example, to form electrical component 100-1 of FIG. 1, the process 200 can include steps 214-1, 216-1, 218-1, and 220-1. Further, for example, to form electrical component 100-2 of FIG. 2, the process 200 can include steps 214-2, 218-2, and 220-2. Other combinations of such steps can be performed to form similar electrical components. For example, to form an electrical component that includes both anode electrodes 102-1 and 102-2, each of steps 214-1, 214-2, 216-1, 218-1, 218-2, and 220-2 may be performed.

At 214-1 or 214-2, a portion of the cathode connection layer 112 can be removed using any suitable technique or techniques, e.g., wet-etching, dry-etching, lasering, etc. In one or more embodiments, the removed the portion of the cathode connection layer 112 provides a separate cathode connection layer for each of the one or more cavities 117. At 214-2 the first major surface 116 of the substrate 104 can be prepared for anode pad 102-2 to be disposed. Preparing the first major surface 116 of the substrate 104 may include at least one of removing oxide, polishing, etching, etc.

At 216-1, the anode connection layer 126 can be disposed on the second major surface 118 of the substrate 104 using any suitable technique or techniques, e.g., deposition, chemical vapor deposition, physical vapor deposition, sputtering, electroplating, printing, dispensing, etc. At 218-1, the cathode packaging layer 108 can be disposed on the cathode conductor layer 110. Additionally, at 218-1, the anode conductor layer 128 can be disposed on the anode connection layer 126. The cathode packaging layer 108 and the anode conductor layer 128-1 can be disposed using any suitable technique or techniques, e.g., deposition, chemical vapor deposition, physical vapor deposition, sputtering, electroplating, printing, dispensing, etc. At 218-2 the anode conductor layer 128-2 can be disposed on the first major surface 116 of the substrate 104. The anode conductor layer 128-2 can be disposed using any suitable technique or techniques, e.g., deposition, chemical vapor deposition, physical vapor deposition, sputtering, electroplating, printing, dispensing, etc.

At 220-1, the electronic devices 100-1 can be singulated using any suitable technique or techniques, e.g., cutting, dicing, sawing, laser cutting, etc. In one or more embodiments, singulating the electronic devices 100-1 may include removing a portion of the substrate 104 and the anode electrode 102-1. At 220-2, the electronic devices 100-2 can be singulated using any suitable technique or techniques, e.g., cutting, dicing, sawing, laser cutting, etc. In one or more embodiments, singulating the electronic devices 100-2 may include removing a portion of the substrate 104 and the anode electrode 102-2.

Figure 5:
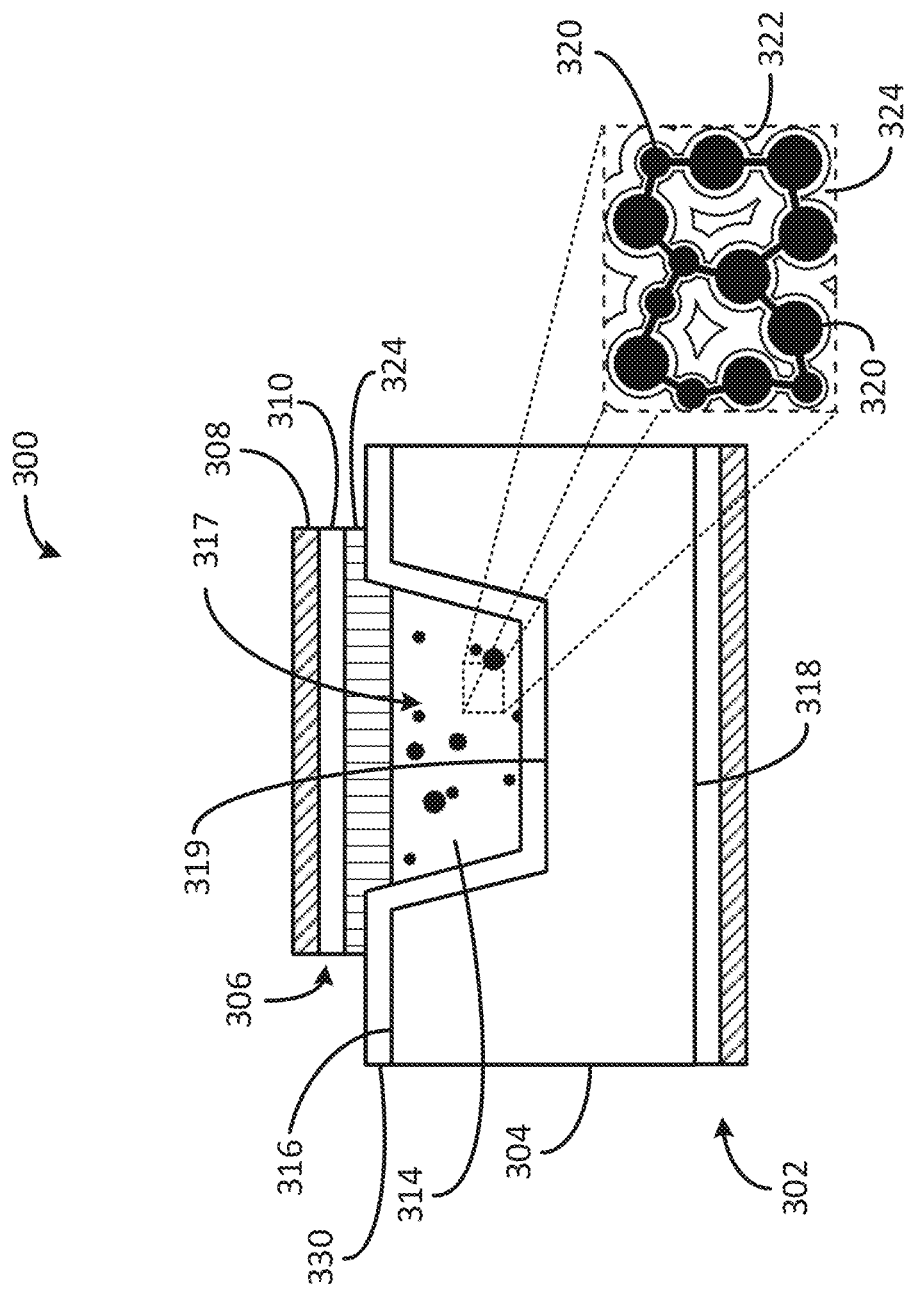
FIG. 5 is a schematic cross-section view of another embodiment of an electrical component.

FIG. 5 is a schematic cross-section view of another embodiment of an electrical component 300. All of the design considerations and possibilities regarding the electrical component 100 of FIG. 1 apply equally to the electrical component 300 of FIG. 5. Electrical component 300 includes a substrate 304 having a first major surface 316, a second major surface 318, and a cavity 317 disposed in the substrate and extending between the first major surface 316 and a recessed surface 319. The electrical component 300 also includes tantalum material 314 disposed within the cavity 317, where the tantalum material includes tantalum particles 320. Further, the electrical component 300 includes an anode electrode 302 disposed on the second major surface 318 of the substrate 304 and a cathode electrode 306 disposed on an electrolyte cathode layer 324 over the cavity 317.

In one or more examples, the substrate 304 is N-type silicon. As used herein, N-type silicon refers to silicon that has been chemically combined (e.g., doped) with another element or material (e.g., phosphorus) to make the silicon electrically conductive (e.g., resistivity of 200 ohm centimeter or less).

One difference between the electrical component 300 and the electrical component 100 is that component 300 includes a tantalum layer 330 disposed on the first major surface 316 and surfaces of the cavity 317 including recessed surface 319. The tantalum layer 330 can be disposed using any suitable technique or techniques, e.g., deposition, chemical vapor deposition, physical vapor deposition, sputtering, electroplating, printing, dispensing, etc. In one or more embodiments, the tantalum layer 330 has a thickness of 1 micrometer to 2 micrometers.

Another difference between the electrical component 300 and the electrical component 100 is that component 300 includes an electrolyte cathode layer 324 that extends over at least a portion of the tantalum layer 330 that is disposed on the first major surface 316. In other words, the electrolyte cathode layer 324, in addition to being disposed on a dielectric layer 322 and filling spaces within the tantalum material 314, can extend above the tantalum material 314 and the tantalum layer 330. Furthermore, the cathode electrode 306 can be disposed on the electrolyte cathode layer 324 and over the cavity 317. In one or more embodiments, a cathode connection layer 310 can be disposed on the electrolyte cathode layer 324 and over the cavity 317. Furthermore, a cathode conductor layer 108 can be disposed on the cathode connection layer 310.

Figure 6:
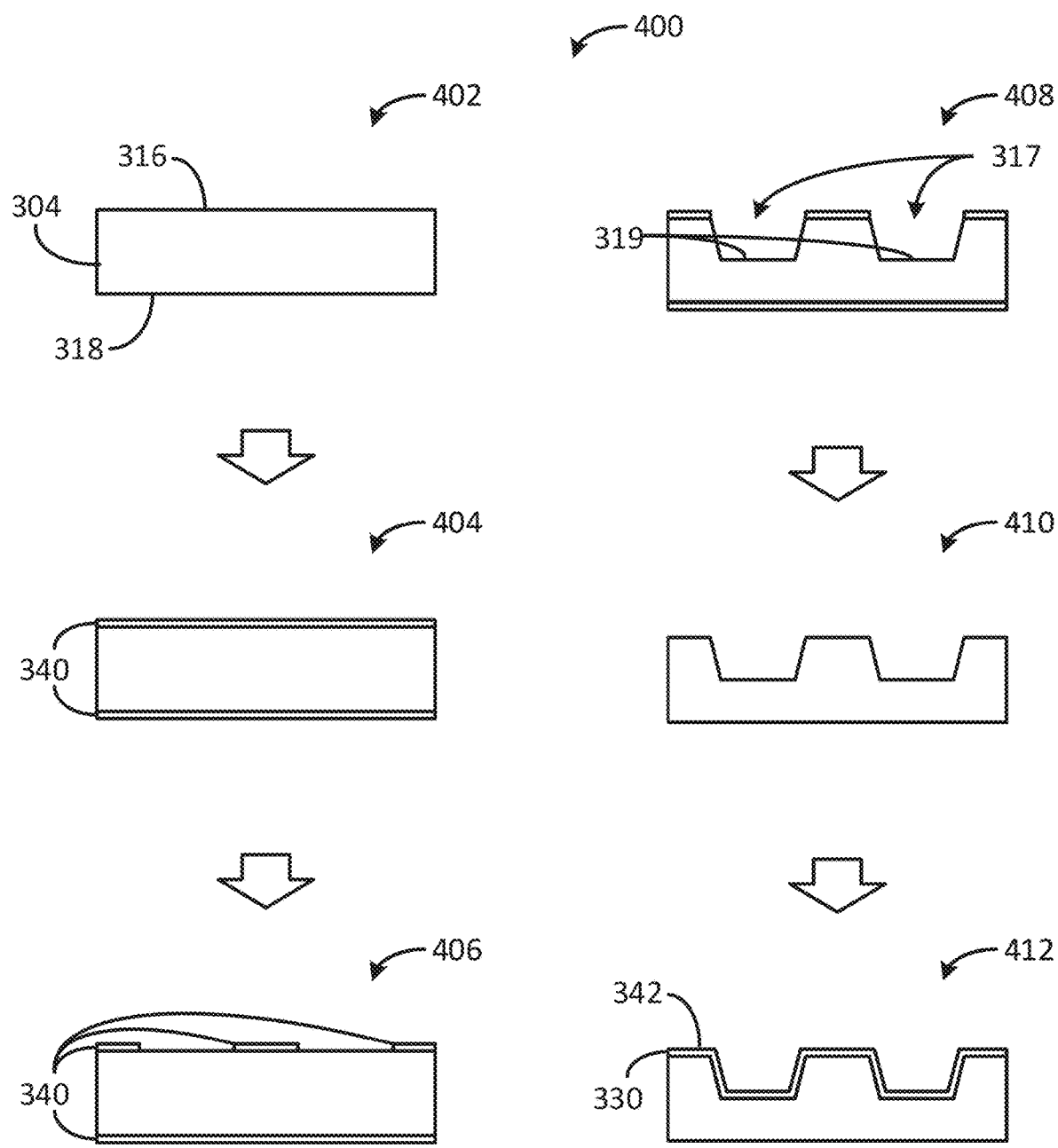
FIG. 6 is a schematic flow diagram of a first portion of a process for forming the electrical component of FIG. 5.
Figure 7:
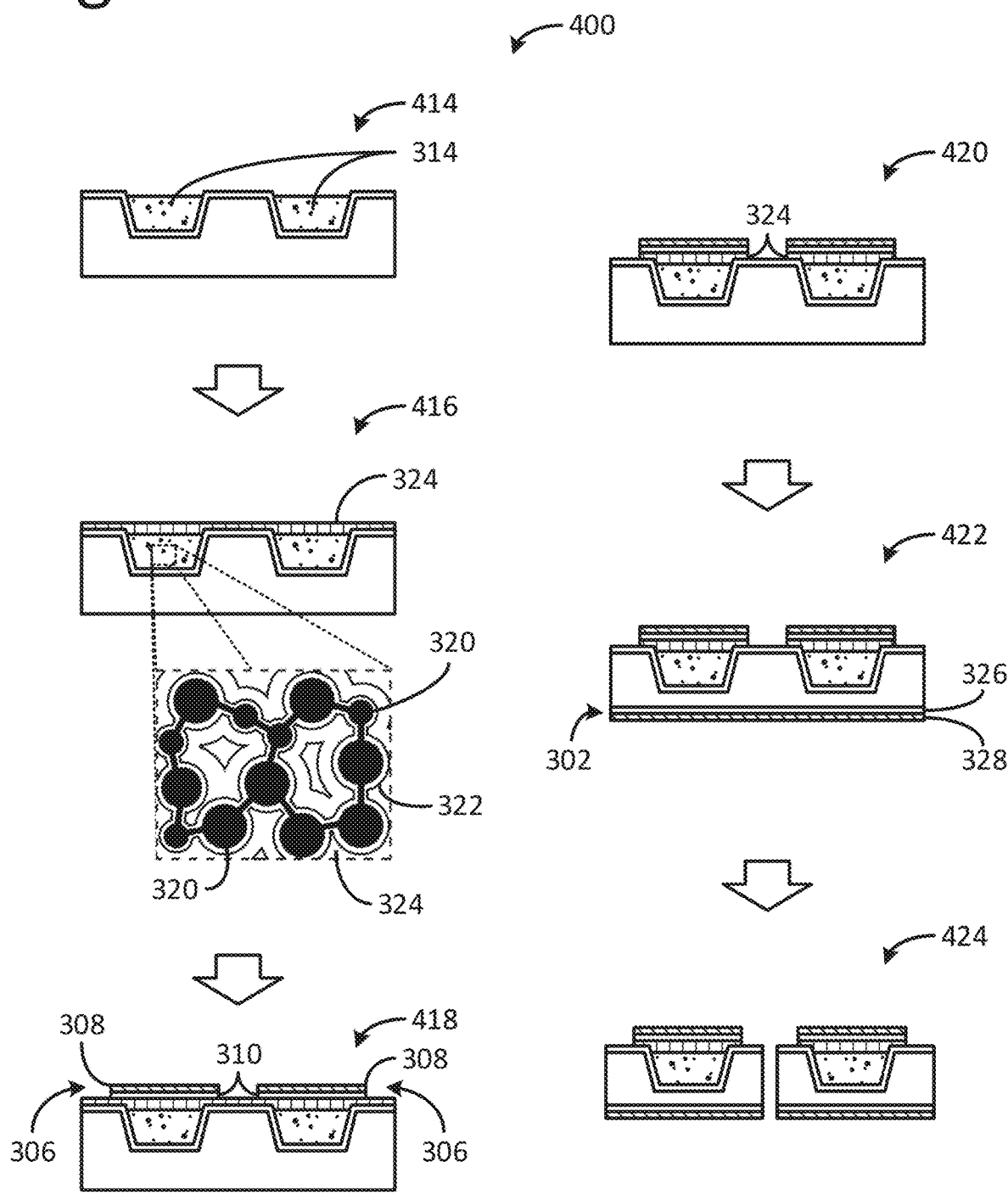
FIG. 7 is a schematic flow diagram of a second portion of a process for forming the electrical component of FIG. 5.

The electrical component 300 can be manufactured utilizing any suitable technique or techniques. For example, FIGS. 6 and 7 are a schematic flow diagrams of first and second portions of one embodiment of a method 400 of forming a plurality of electrical components 300. Although described in reference to electrical component 300 of FIG. 5, the method 400 can be utilized to form any suitable electrical component.

At 402, a substrate 304 is provided. The substrate 304 included the first major surface 316 and the second major surface 318 opposite the first major surface. The substrate 304 can include any suitable conductive material, e.g., tantalum foil, niobium foil, silicon, N-type silicon, metal foil, metal alloy foil, etc. In one or more examples, the substrate 304 is N-type silicon. The substrate 304 may be provided in any suitable size and any suitable thickness. In one or more embodiments, the substrate 304 may be provided at a thickness between 50 micrometers to 625 micrometers.

At 404, a field oxide hard mask 340 can be disposed on at least one of the first major surface 316 or the second major surface 318 of the substrate 304. The field oxide hard mask 340 may be disposed using any suitable technique or techniques, e.g., growing, deposition, sputtering, etc. At 406, one or more portions of the field oxide hard mask 340 may be removed. The portions of the field oxide hard mask 340 may be removed using any suitable technique or techniques, e.g., etching, lasering, etc.

At 408, one or more cavities 317 can be disposed in the first major surface 316 of the substrate 304 using any suitable technique or techniques, e.g., anisotropic-etching, wet-etching, lasering, sawing, etc. In one or more embodiments, the one or more cavities 317 may be formed using anisotropic etching. Each of the one or more cavities 317 may extend from the first major surface 316 to the recessed surface 319. Each of the one or more cavities 317 may have a depth measured from the first major surface 316 to the recessed surface 319 that is 20 percent to 90 percent of the thickness of the substrate 304. In one or more embodiments, the depth of the one or more cavities 317 may be 100 micrometers to 250 micrometers. At 410, the field oxide hard mask 340 can be removed from the substrate 304 using any suitable technique or techniques, e.g., wet etching, dry etching, lasering, etc.

At 412, the tantalum layer 330 can be disposed on the first major surface 316 and the recessed surface 319 using any suitable technique or techniques, e.g., deposition, PVD, CVD, sputtering, electroplating, foil lamination, etc. In one or more embodiments, the tantalum layer 330 is disposed with a thickness of 1 micrometer to 2 micrometers. Furthermore, an oxide layer 342 can be disposed on the tantalum layer 330 using any suitable technique or techniques, at 412. In one or more embodiments, the oxide layer 342 may be disposed by placing the substrate 304 in an oxygen rich environment and heating the substrate and the tantalum layer 330. The substrate 304 and tantalum layer 330 may be heated to at least 500 degrees Celsius for at least 10 minutes. Subsequent to the oxide layer 342 being disposed, the substrate 304, the tantalum layer 330, and the oxide layer 342 may be annealed to drive the oxide layer into the tantalum layer. Annealing may include heating to at least 600 degrees Celsius for at least 10 minutes.

At 414, the tantalum material 314 including tantalum particles 320 can be disposed in the one or more cavities 317 of the substrate 304 using any suitable technique or techniques. The tantalum material 314 may include, e.g., tantalum powder, a tantalum slug, tantalum paste, etc. In embodiments where the tantalum material 314 includes tantalum paste, the tantalum paste can be dried and debindered using any suitable technique or techniques at 414, for example, heating the tantalum paste.

In one or more embodiments, the tantalum material 314 can be sintered at 414 of FIG. 7 using any suitable technique or techniques. Sintering the tantalum material 314 can cause the tantalum particles 320 to at least partially fuse together to form one or more mechanical and electrical connections between the tantalum particles. Additionally, sintering can cause one or more of the tantalum particles 314 to fuse to the substrate 304, forming at least one mechanical and electrical connection between the tantalum material and the substrate. In one or more embodiments, the tantalum material 314 can be sintered by heating the material to a temperature of at least 3400 degrees Celsius and no greater than 3000 degrees Celsius. In one or more embodiments, the tantalum material 314 can be pressed and sintered at 414.

At 416, the dielectric layer 322 can be disposed on the tantalum particles 320 using any suitable technique or techniques. In one or more embodiments, the dielectric layer 322 may be disposed using, e.g., anodization, wet-forming, atomic layer deposition, annealing, etc. The dielectric layer 322 can include any suitable dielectric material or materials, e.g., tantalum pentoxide. Further, at 416, an electrolyte cathode layer 324 can be disposed on the dielectric layer 322 using any suitable technique or techniques. In one or more embodiments, the electrolyte cathode layer 324 may be disposed using, e.g., pyrolysis, press, laser sizing, printing, dispensing, dip-coating, etc. The electrolyte cathode layer 324 can include any suitable material or materials, e.g., manganese dioxide, conductive polymer, etc. In one or more embodiments, the electrolyte cathode layer 324 is disposed over at least a portion of the tantalum layer 330 disposed on the first major surface 316. In other words, the electrolyte cathode layer 324, in addition to being disposed on the electrolyte cathode layer 324 and filling spaces within the tantalum material, can be disposed such that the electrolyte cathode layer extends above the tantalum material 314 and the tantalum layer 330.

At 418, one or more cathode electrodes 306 can be disposed on the electrolyte cathode layer 324 and over the one or more cavities 317 using any suitable technique or techniques, e.g., deposition, PVD, CVD, sputtering, electroplating, foil lamination, etc. In one or more embodiments, disposing each of the one or more cathode electrodes 306 includes disposing the cathode connection layer 310 and the cathode conductor layer 308. The cathode connection layer 310 may be disposed on the electrolyte cathode layer 324 and the one or more cavities 317 using any suitable technique or techniques, e.g., deposition, PVD, CVD, sputtering, electroplating, foil lamination, etc. The cathode conductor layer 308 may be disposed on the cathode connection layer 310 using any suitable technique or techniques, e.g., deposition, PVD, CVD, sputtering, electroplating, foil lamination, shadow masking, etc.

At 420, a portion of the electrolyte cathode layer 324 can be removed. The portion of the electrolyte cathode layer 324 may be removed using any suitable technique or techniques, e.g., wet-etching, dry-etching, lasering, etc. In one or more embodiments, removal of the portion of the electrolyte cathode layer 324 provides a separate electrolyte cathode layer for each of the one or more cavities 317. Furthermore, the substrate 304 may be thinned at 420 using any suitable technique or techniques, e.g., grinding, cutting, lasering, etc.

At 422, the anode electrode 302 can be disposed on the second major surface 318 of the substrate 304 using any suitable technique or techniques, e.g., deposition, chemical vapor deposition, physical vapor deposition, sputtering, electroplating, printing, dispensing, etc. In one or more embodiments, disposing the anode electrode 302 includes disposing an anode connection layer 326 and an anode conductor layer 328. The anode connection layer 326 may be disposed on the second major surface 318 of the substrate 304 using any suitable technique or techniques, e.g., deposition, chemical vapor deposition, physical vapor deposition, sputtering, electroplating, printing, dispensing, etc. The anode conductor layer 328 can be disposed on the anode connection layer 326 using any suitable technique or techniques, e.g., deposition, chemical vapor deposition, physical vapor deposition, sputtering, electroplating, printing, dispensing, etc.

At 424, the electronic devices 300 can be singulated using any suitable technique or techniques, e.g., cutting, dicing, sawing, laser cutting, etc. In one or more embodiments, singulating the electronic devices 300 may include removing a portion of the substrate 304 and the anode electrode 302.

Figure 8:
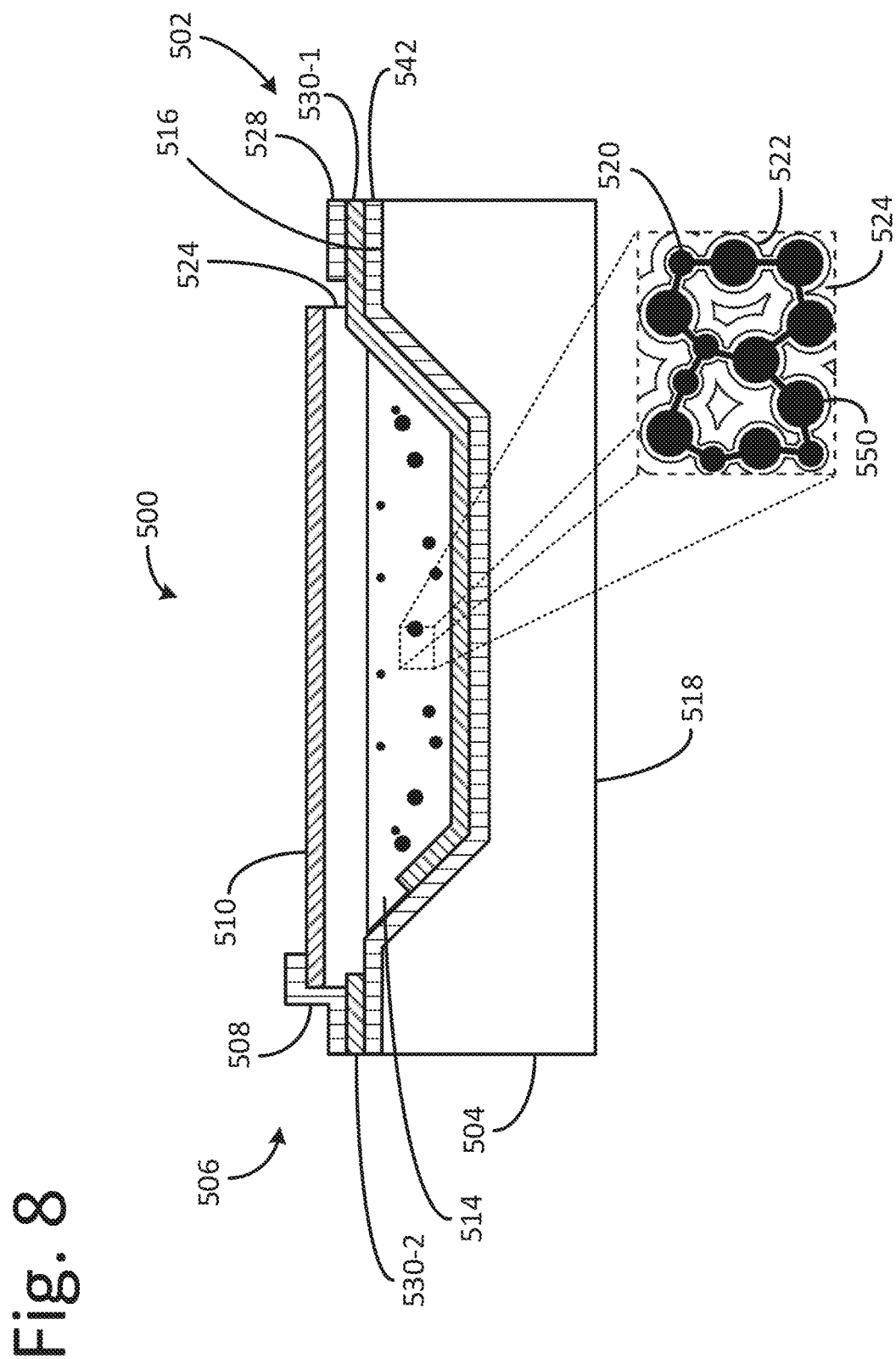
FIG. 8 is a schematic cross-section view of another embodiment of an electrical component.

FIG. 8 is a schematic cross-section view of another embodiment of an electrical component 500. All of the design considerations and possibilities regarding the electrical component 100 of FIG. 1 and the electrical component 300 of FIG. 5 apply equally to the electrical component 500 of FIG. 8. Electrical component 500 includes a substrate 504 having a first major surface 516, a second major surface 518, and a cavity 517 disposed in the substrate and extending between the first major surface 516 and a recessed surface 519. The electrical component 500 also includes tantalum material 514 disposed within the cavity 517, where the tantalum material includes tantalum particles 520. Further, the electrical component 500 includes an anode electrode 502 disposed over a portion of the first major surface 516 of the substrate 504 and a cathode electrode 506 disposed over another portion of the first major surface 516 of the substrate.

One difference between the electrical component 500 and electrical component 100 is that component 500 includes an oxide layer 542 disposed on the first major surface 516 and surfaces of the cavity 517 including recessed surface 519. The oxide layer 542 can be disposed using any suitable techniques, e.g., growing, deposition, sputtering, etc. The oxide layer 542 may be an electrical insulator.

Another difference between the electrical component 500 and the electrical component 100 is that component 500 includes a first tantalum layer 530-1 and second tantalum layer 530-2 (referred to collectively as tantalum layers 530) disposed on the oxide layer 542. The tantalum layers 530 can be disposed using any suitable technique or techniques, e.g., deposition, chemical vapor deposition, physical vapor deposition, sputtering, electroplating, printing, dispensing, etc. In one or more embodiments, the tantalum layers 530 have a thickness of 1 micrometer to 2 micrometers. The first tantalum layer 530-1 and the second tantalum layer 530-2 may be separated by tantalum material 520 and electrolyte cathode layer 524. The first tantalum layer 530-1 may extend over portions of the oxide layer 542 that extend over the first major surface 516 and into the cavity 517 over the recessed surface 519. The second tantalum layer 530-2 may extend over portions of the oxide layer 542 that extend over the first major surface 516.

Another difference between the electrical component 500 and the electrical component 100 is that electrolyte cathode layer 524, in addition to being disposed on the dielectric layer 522 and filling spaces within the tantalum material, can extend above the tantalum material 514 and over at least a portion of the tantalum layers 530 and the oxide layer 542.

Another difference between the electrical component 500 and the electrical component 100 is that component 500 includes anode pad 528 disposed on a portion of the first tantalum layer 530-1. The anode pad 528 and the first tantalum layer 530-1 may form the anode electrode 502. The anode pad 528 can include any suitable electrically conductive material or materials, e.g., copper, gold, silver, tantalum, graphite, aluminum, chrome, carbon, etc. The anode pad 528 can include any suitable dimensions and take any suitable shape or shapes. Further, the anode pad 528 can be formed using any suitable technique or techniques, e.g., deposition, chemical vapor deposition, physical vapor deposition, sputtering, electroplating, printing, dispensing, etc. The anode pad 528 may be disposed on a portion of the first tantalum layer 530-1 that resides over the first major surface 516 of the substrate 504.

Further, the electrical component 500 can also include a cathode pad 508 disposed on portions of the second tantalum layer 530-2 and a cathode connection layer 510. The cathode pad 508 and the cathode connection layer 510 may form the cathode electrode 506. The cathode pad 508 can include any suitable dimensions and take any suitable shape or shapes. The cathode pad 508 can include any suitable electrically conductive material or materials, e.g., copper, gold, silver, aluminum, or other conductive material. The cathode pad 508 can be formed using any suitable technique, e.g., deposition, PVD, CVD, sputtering, electroplating, foil lamination, etc.

Figure 9:
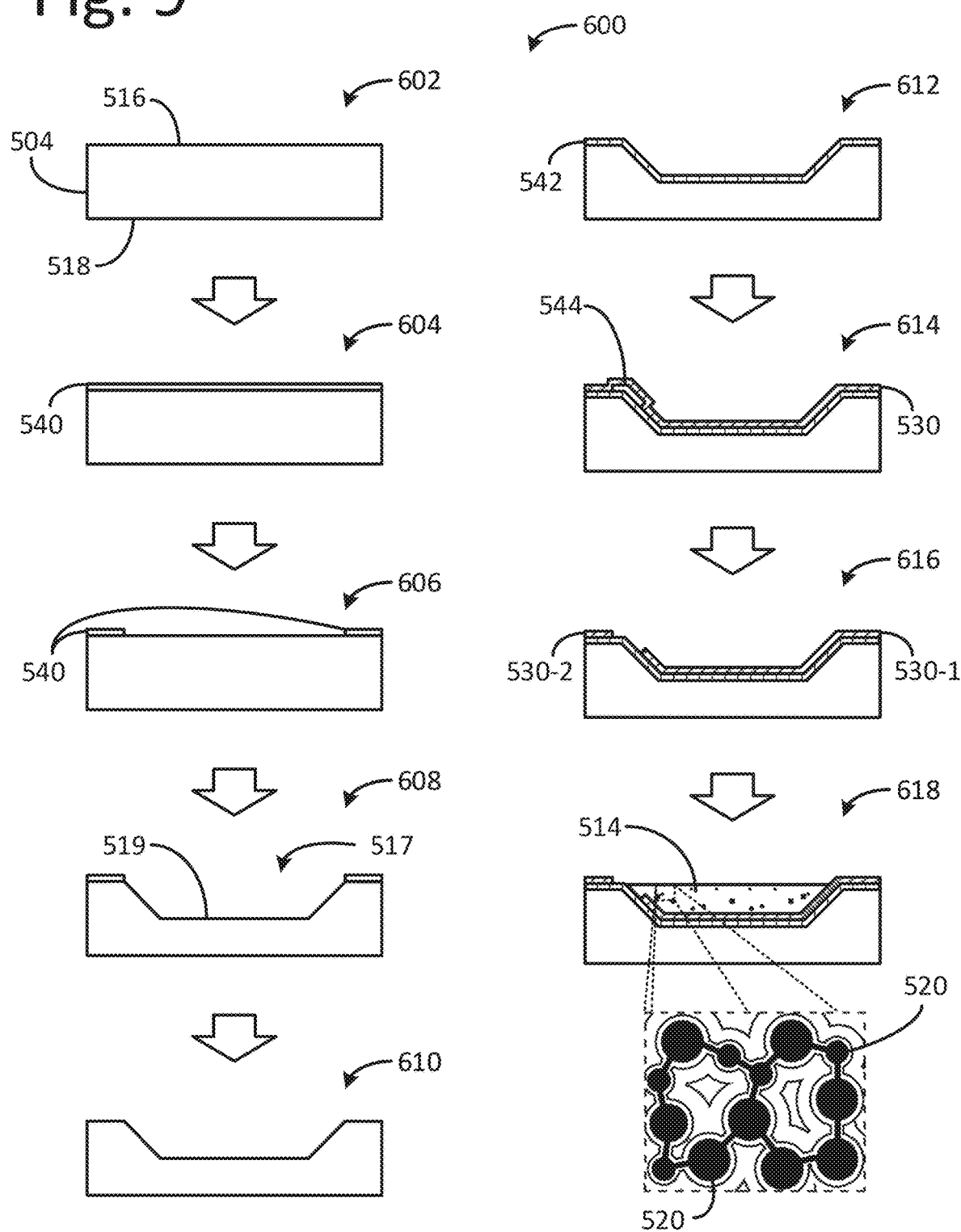
FIG. 9 is a schematic flow diagram of a first portion of a process for forming the electrical component of FIG. 8.
Figure 10:
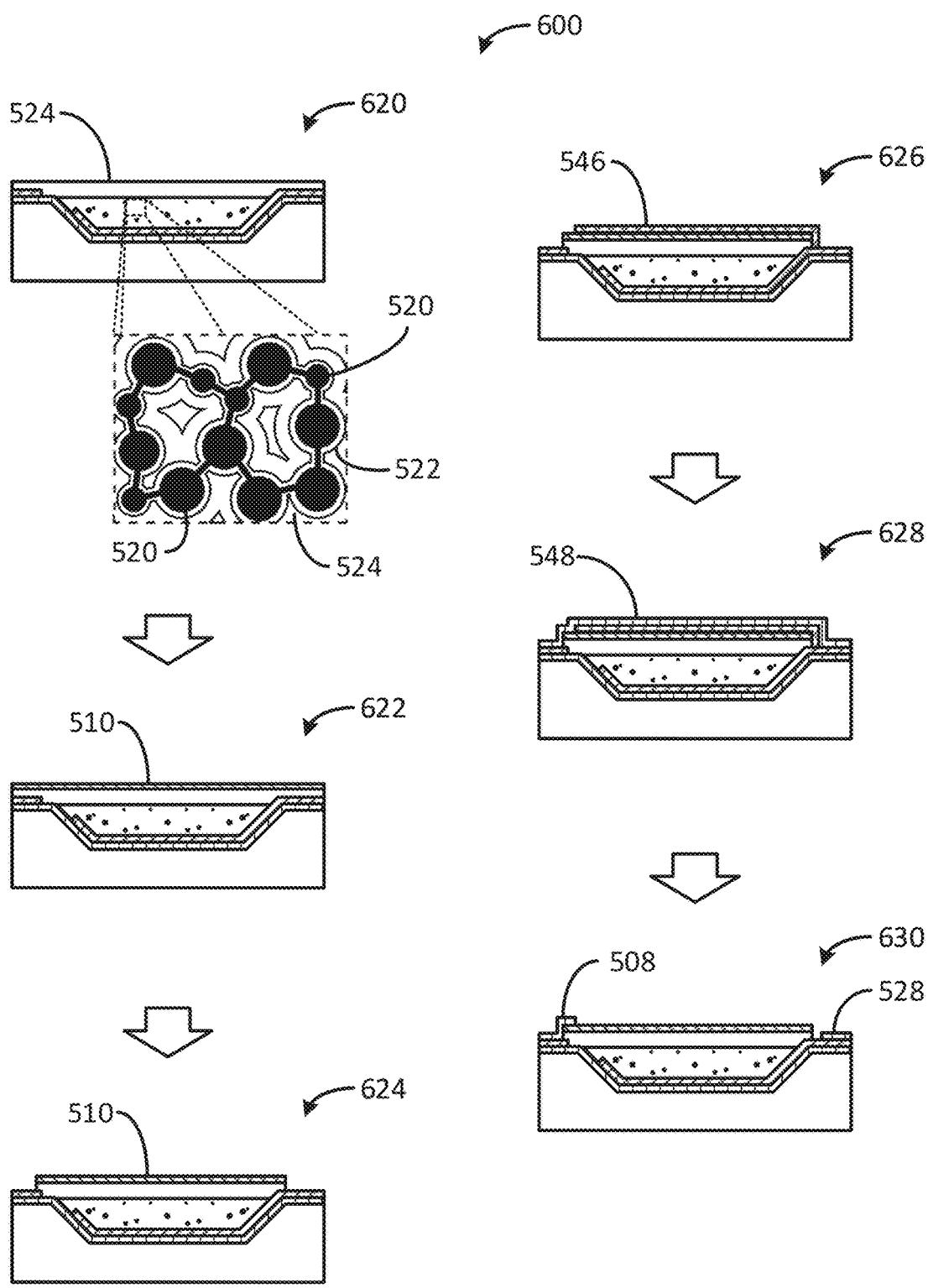
FIG. 10 is a schematic flow diagram of a second portion of a process for forming the electrical component of FIG. 8.

The electrical component 500 can be manufactured utilizing any suitable technique or techniques. For example, FIGS. 9 and 10 are schematic flow diagrams first and second portions of one embodiment of a method 600 of forming a plurality of electrical components 500. Although described in reference to electrical component 500 of FIG. 8, the method 600 can be utilized to form any suitable electrical component.

At 602, the substrate 504 is provided. The substrate 504 includes the first major surface 516 and the second major surface 518 opposite the first major surface. The substrate 504 can include any suitable material, e.g., tantalum foil, silicon, N-type silicon, glass, ceramic, etc. In one or more examples, the substrate 504 is N-type silicon. The substrate 504 may be provided in any suitable size and any suitable thickness. The substrate 504 may be provided at a thickness between 50 micrometers to 625 micrometers.

At 604, a field oxide hard mask 540 can be disposed on the first major surface 516 of the substrate 504. The field oxide hard mask 540 may be disposed using any suitable technique or techniques, e.g., growing, deposition, sputtering, etc. At 606, one or more portions of the field oxide hard mask 540 may be removed. The portions of the field oxide hard mask 540 may be removed using any suitable technique or techniques, e.g., etching, lasering, etc.

At 608, one or more cavities 517 can be disposed in the first major surface 516 of the substrate 504 using any suitable technique or techniques, e.g., anisotropic-etching, wet-etching, lasering, sawing, etc. In one or more embodiments, the one or more cavities 517 may be formed using anisotropic etching. The one or more cavities 517 may extend from the first major surface 516 to a recessed surface 519. The one or more cavities 517 may have a depth measured from the first major surface 516 to the recessed surface 519 that is 20 percent to 90 percent of the thickness of the substrate 504. In one or more embodiments, the depth of the one or more cavities 517 may be 100 micrometers to 250 micrometers. At 610, the field oxide hard mask 540 can be removed from the substrate 504 using any suitable technique or techniques, e.g., wet etching, dry etching, lasering, etc.

At 612, an oxide layer 542 can be disposed on the first major surface 516 of the substrate 504 and surfaces of the cavity 517 including the recessed surface 519 using any suitable technique or techniques, at 612. In one or more embodiments, the oxide layer 542 may be disposed by growing the oxide layer in a diffusion furnace containing water vapor (e.g., wet oxide growth) at a temperature between 1000 degrees Celsius and 1200 degrees Celsius. In one or more embodiments, the oxide layer 542 may be disposed by placing the substrate 504 in an oxygen rich environment and heating the substrate. The substrate 504 may be heated to at least 500 degrees Celsius for at least 10 minutes.

At 614, photoresist 544 can be disposed on a portion of the oxide layer 542 and a tantalum layer 530 can be disposed on the oxide layer and the photoresist. The photoresist 544 can be disposed using any suitable technique or techniques, e.g., spray coating, sputtering, laminating, etc. The photoresist 544 may be developed prior to the tantalum layer 530 being disposed. The tantalum layer 530 can be disposed using any suitable technique or techniques, e.g., deposition, PVD, CVD, sputtering, electroplating, foil lamination, etc. In one or more embodiments, the tantalum layer 530 is disposed with a thickness of 1 micrometer to 2 micrometers. At 616, the photoresist 544 may be removed along with a portion of the tantalum layer 530 disposed on the photoresist thereby separating the tantalum layer 530 into the first tantalum layer 530-1 and the second tantalum layer 530-2.

At 618, the tantalum material 514 including tantalum particles 520 can be disposed into the one or more cavities 517 of the substrate 504 using any suitable technique or techniques. The tantalum material 514 may include, e.g., tantalum powder, a tantalum slug, tantalum paste, etc. In embodiments where the tantalum material 517 includes tantalum paste, the tantalum paste can be dried and debindered using any suitable technique or techniques at 618, for example, heating the tantalum paste.

In one or more embodiments, the tantalum material 514 can be sintered at 618 using any suitable technique or techniques. Sintering the tantalum material 514 can cause the tantalum particles 520 to at least partially fuse together to form one or more mechanical and electrical connections between the tantalum particles. Additionally, sintering can cause one or more of the tantalum particles 514 to fuse to the substrate 504, forming at least one mechanical and electrical connection between the tantalum material and the substrate. In one or more embodiments, the tantalum material 514 can be sintered by heating the material to a temperature of at least 1200 degrees Celsius and no greater than 3000 degrees Celsius.

At 620 of FIG. 10, the dielectric layer 522 can be disposed on the tantalum particles 520 using any suitable technique or techniques. In one or more embodiments, the dielectric layer 522 may be disposed using, e.g., anodization, wet-forming, atomic layer deposition, annealing, etc. The dielectric layer 522 can include any suitable dielectric material or materials, e.g., tantalum pentoxide. Further, at 608, an electrolyte cathode layer 524 can be disposed on the dielectric layer 522 using any suitable technique or techniques. In one or more embodiments, the electrolyte cathode layer 524 may be disposed using, e.g., pyrolysis, press, printing, dispensing, dip-coating, etc. The electrolyte cathode layer 524 can include any suitable material or materials, e.g., manganese dioxide, conductive polymer, etc. In one or more embodiments, the electrolyte cathode layer 524 is disposed over at least a portion of the tantalum layer 530 disposed on the first major surface 516. In other words, the electrolyte cathode layer 524, in addition to being disposed on the electrolyte cathode layer 524 and filling spaces within the tantalum material 514, can be disposed such that the electrolyte cathode layer extends above the tantalum material and the tantalum layers 530.

At 622, the cathode connection layer 510 can be disposed on the electrolyte cathode layer 524 and over the cavity 517 using any suitable technique or techniques, e.g., deposition, PVD, CVD, sputtering, electroplating, foil lamination, etc. At 624 a portion of the electrolyte cathode layer 524 and the cathode connection layer 510 can be removed using any suitable technique or techniques, e.g., wet etching, dry etching, lasering, etc. Removal of the portion of the electrolyte cathode layer 524 and the cathode connection layer 510 may expose surfaces of the tantalum layers 530.

At 626, photoresist 546 can be disposed on a portion of the first tantalum layer 530-1 and a portion of the cathode connection layer 510 using any suitable technique or techniques, e.g., spray coating, spin coating, sputtering, etc. Photoresist 546 may be developed at 626. At 628, a conductive layer 548 is disposed on portions of the tantalum layers 530, on the photoresist 546, and on a portion of the cathode connection layer 510 using any suitable technique or techniques, e.g., deposition, PVD, CVD, sputtering, electroplating, foil lamination, etc. At 630, the photoresist 546 and portions of the conductive layer 548 can be removed. The portions of the conductive layer 548 that remain form the anode pad 528 on the first tantalum layer 530-1 and a cathode pad 508 on portions of the second tantalum layer 530-2 and cathode connection layer 510.

Figure 11:
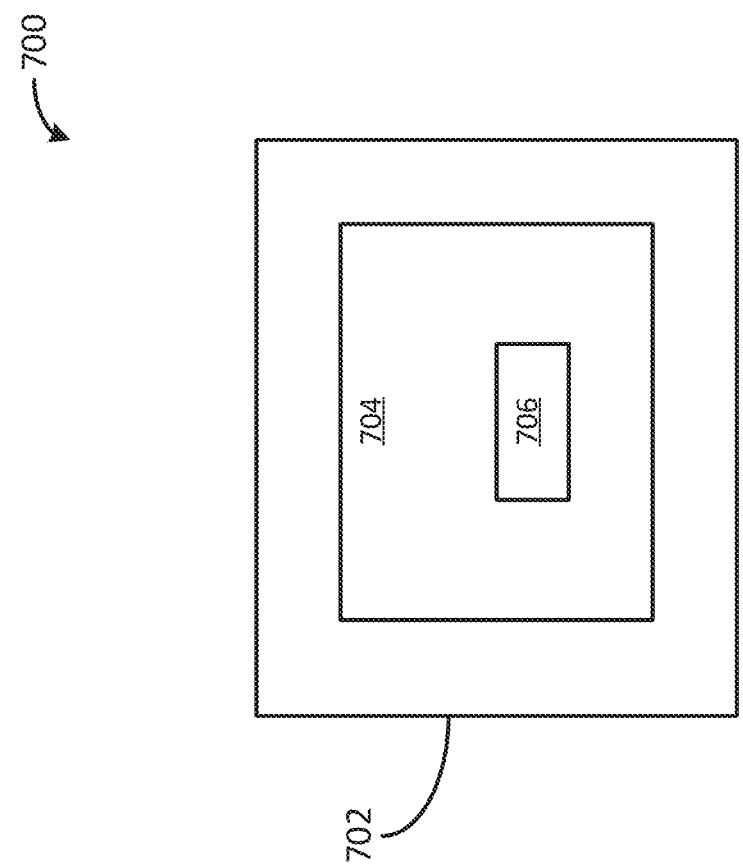
FIG. 11 is a schematic diagram of an implantable medical device including an electrical component as described herein.

The electrical components 100, 300, 500 as described herein can be included in any suitable implantable medical devices. For example, FIG. 11 is a schematic diagram of an implantable medical device 700. Implantable medical device 700 includes a housing 702 and a circuit electronic assembly 704 within the housing. The electronic assembly 704 can include an electrical component 706. The electrical component 706 can be any one of the electrical components 100, 300, and 500 as described herein.

The implantable medical device 700 can include any suitable medical device. In one or more embodiments, the implantable medical device 700 can include an implantable defibrillator.

It should be understood that various aspects disclosed herein can be combined in different combinations than the combinations specifically presented in the description and accompanying drawings. It should also be understood that, depending on the example, certain acts or events of any of the processes or methods described herein can be performed in a different sequence, can be added, merged, or left out altogether (e.g., all described acts or events cannot be necessary to carry out the techniques). In addition, while certain aspects of this disclosure are described as being performed by a single module or unit for purposes of clarity, it should be understood that the techniques of this disclosure can be performed by a combination of units or modules associated with, for example, a medical device.

In one or more examples, the described techniques can be implemented in hardware, software, firmware, or any combination thereof. If implemented in software, the functions can be stored as one or more instructions or code on a computer-readable medium and executed by a hardware-based processing unit. Computer-readable media can include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions can be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein can refer to any of the foregoing structure or any other physical structure suitable for implementation of the described techniques. Also, the techniques could be fully implemented in one or more circuits or logic elements.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. An electrical component comprising:
   a substrate comprising a first major surface, a second major surface, and a cavity disposed in the substrate and extending between the first major surface and a recessed surface;

tantalum material disposed within the cavity and comprising tantalum particles;
a dielectric layer disposed on the tantalum particles;
an electrolyte cathode layer disposed on the dielectric layer; and
a cathode electrode disposed over the cavity.

2. The electrical component of claim 1, wherein the substrate comprises tantalum foil.

3. The electrical component of claim 2, wherein the tantalum foil substrate comprises a thickness of at least 50 micrometers and no greater than 300 micrometers.

4. The electrical component of claim 1, further comprising a tantalum layer disposed on the first major surface of the substrate and the recessed surface of the substrate between the tantalum particles and the recessed surface.

5. The electrical component of claim 1, further comprising an anode connector layer disposed on the second major surface of the substrate.

6. The electrical component of claim 1, further comprising an insulator layer disposed on the first major surface of the substrate and the recessed surface of the substrate between the tantalum particles and the recessed surface.

7. A method comprising:
disposing a cavity in a substrate that extends between a first major surface and a recessed surface;
disposing tantalum material in the cavity, the tantalum material comprising tantalum particles;
disposing a dielectric layer on the tantalum particles;
disposing an electrolyte cathode layer on the dielectric layer; and
disposing a cathode electrode on the electrolyte cathode layer and over the cavity.

8. The method of claim 7, further comprising disposing a tantalum layer on the first major surface of the substrate and the recessed surface of the substrate prior to disposing the tantalum material in the cavity.

9. The method of claim 8, further comprising:
disposing an oxide layer on the tantalum layer; and
annealing the tantalum layer and the oxide layer prior to disposing the tantalum material in the cavity.

10. The method of claim 7, further comprising disposing an anode electrode on a second major surface of the substrate.

11. The method of claim 7, further comprising disposing an insulator layer on the first major surface of the substrate and the recessed surface prior to disposing the tantalum material in the cavity.

12. The method of claim 7, further comprising sintering the tantalum particles prior to disposing the dielectric layer.

13. An implantable medical device comprising:
a housing; and
an electronic assembly within the housing and comprising an electrical component, the electrical component comprising:
a substrate comprising a first major surface, a second major surface, and a cavity disposed in the substrate and extending between the first major surface and a recessed surface;
tantalum material disposed within the cavity and comprising tantalum particles;
a dielectric layer disposed on the tantalum particles;
an electrolyte cathode layer disposed on the dielectric layer; and
a cathode electrode disposed over the cavity.

14. The implantable medical device of claim 13, wherein the substrate comprises tantalum foil.

15. The implantable medical device of claim 14, wherein the tantalum foil substrate comprises a thickness of at least 50 micrometers and no greater than 300 micrometers.

16. The implantable medical device of claim 13, wherein the substrate comprises silicon.

17. The implantable medical device of claim 13, further comprising a tantalum layer disposed on the first major surface of the substrate and the recessed surface of the substrate between the tantalum particles and the recessed surface.

18. The implantable medical device of claim 13, further comprising an anode connector layer disposed on the second major surface of the substrate.

19. The implantable medical device of claim 13, further comprising an insulator layer disposed on the first major surface of the substrate and the recessed surface of the substrate between the tantalum particles and the recessed surface.

20. The implantable medical device of claim 19, further comprising a tantalum layer disposed on at least a portion of the insulator layer.

* * * * *